United States Patent
Yuasa

[11] Patent Number: 6,036,649
[45] Date of Patent: Mar. 14, 2000

[54] ULTRASOUND PROBE

[75] Inventor: Katsutoshi Yuasa, Otawara, Japan

[73] Assignee: Kabushiki Kaisha Toshiba, Kawasaki, Japan

[21] Appl. No.: 09/081,018

[22] Filed: May 19, 1998

[30]      Foreign Application Priority Data

Jun. 17, 1997   [JP]   Japan ................................ 9-159796

[51] Int. Cl.⁷ .................................................. A61B 8/00
[52] U.S. Cl. ........................................... 600/462; 600/464
[58] Field of Search .................................. 600/459, 461, 600/464, 462, 437

[56]              References Cited

U.S. PATENT DOCUMENTS

| | | | |
|---|---|---|---|
| 4,883,059 | 11/1989 | Stedman et al. | 600/459 |
| 5,090,414 | 2/1992 | Takano | 600/459 |
| 5,235,987 | 8/1993 | Wolfe | 600/459 |

*Primary Examiner*—William E. Kamm
*Assistant Examiner*—Maulin Patel
*Attorney, Agent, or Firm*—Oblon, Spivak, McClelland, Maier & Neustadt, P.C.

[57]                   ABSTRACT

An ultrasound probe of the present invention comprises a rod-like grip section constituting a rear section of the probe, a rod-like insertion section constituting a forward section of the probe and having a piezoelectric element array at a forward end and a slot structure formed parallel to an axis of the grip section. A centesis instrument is put on the slot. This specific arrangement allows the axis of the centesis instrument to be less displaced relative to the axis of the probe, so that the centesis instrument is not unsteady relative to the probe. Further, the centesis instrument ensures readier attachment and detachment to and from the probe simply by putting a body of the instrument on the probe.

14 Claims, 5 Drawing Sheets

ULTRASOUND PROBE

BACKGROUND OF THE INVENTION

The present invention relates to an ultrasound probe which, in use, is inserted into a human body cavity through the endovagine, intestinum rectum, etc.

Currently, the ultrasound diagnosis, being compared to an X-ray computer tomography apparatus, magnetic resonance imaging (MRI) apparatus, gamma camera, etc., is excellent in terms of real time, compact, cost and safety aspects and indispensable in a medical field, in particular, a urology and gynecology. The pulse echo method constitutes one of its main stream. This method is excellent in a distance resolution and enables a cross-sectional structure of a living body to be converted to a visual image.

As well known in the art, however, this method imparts a restriction to the absorption of an ultrasound energy by the living body, its boundary and attenuation wave as well as to its reaching distance. Further, the frame rate has its lower limit set so as to visualize a motion smoothly. These impart a limitation to the depth of a visual field on diagnosis. In order to clearly visualize a deep-seated object of a living body, such as a fetus or prostate gland, the ultrasound probe has been developed and intensively used which is inserted into the living body through the endovagine, rectal, etc., route.

This type of probe has a structure comprising a substantially cylindrical, easier-to-grip part 3 of a proper thickness and a narrow-rod-like insertion part 2 extending from the grip part 3 to ensure ready insertion into the body cavity. A piezoelectric element array 1 is provided at a forward end portion of the insertion part. The grip section 3 has its upper side somewhat cut to provide a flat section 5, so that the operator can grasp the upper and lower sides of the grip section without being so recognized. The probe is carefully water-proofed and formed with a minimal uneven surface to ensure its ready washing and sterilization.

For prostate diagnosis it is probed effective to actually check a sampled tissue. For this reason, the coelom probe has a hook-shaped hole 7 and circular recess 9 so as to allow a centesis adaptor to be mounted thereon as shown in FIG. 2. In order to mount a centesis adaptor on the coelom probe, a hook 8 on the forward end portion of a sheath tube 6 set on a clamp 10 of the centesis adaptor is latched to the hook-shaped hole 9 of the probe and a tight clamp is made with a screw 11 attached to the recess 9.

The operator aims a centesis needle at a target, while looking at an ultrasound image, stabs the needle into the target organ and pulls it back. By doing so, the tissue sample is scraped off the organ in a manner to be deposited within the hook of the forward end portion of the needle.

This type of adaptor is complicated in construction and very difficult to wash and sterilize and sometimes provides an obstacle in a centesis operation. Further, if the centesis adaptor is repeatedly attached and detached to and from the probe, then the recess 9 is worn away, sometimes failing to adequately fix the centesis adaptor to the probe. The serious defect is in that, since some force is needed at each push-out, stabbing and pull-back action, the probe is somewhat shacken, so that the centesis needle is displaced off the target.

In recent years, a centesis instrument (hereinafter referred to as a "Bird Gun"), manufactured by Bird Co, Ltd, has been rapidly accepted in this field. This Bird Gun has a body of a substantially hexagonal prism. A spring and mechanism in this body are so constructed that a centesis needle can be rapidly and forcibly pushed out from the Gun's body and rapidly pulled back from a location where the needle is fully extended out. This increases a probability that this rapid action will ensure accurate stabbing of the needle into a target organ in comparison with a slot manual motion.

The Bird Gun is set to the probe in the following step sequence.

(1) The spring is adequately stretched taut and locked.
(2) The centesis needle somewhat projected from the body is passed through the sheath tube 6 of the centesis adaptor.
(3) The Gun's body is placed on the flat section 5 of the grip section 3 of the probe.

The stabbing step sequence is as follows:

(1) The operator grips the Bird Gun's body and probe by his or her own hands.
(2) The sheath tube, together with the probe's insertion section, is inserted, for example, into the intestinum rectum.
(3) A target is set while looking at an ultrasound image.
(4) A sight of the Bird Gun at a target is adjusted.
(5) A trigger button of the Bird Gun is depressed.
(6) The locking of the spring is released to allow a tissue sample to be scraped off.

Here, the problem with this sequence is that it is difficult for the operator to stably grip the Bird Gun's body, together with the probe, even with both his or her hands. That is, the Bird Gun's body (hexagonal prism) is narrow and not flat and unsteady on the flat section of the probe. Therefore, there is the inconvenience of having to readjust the sighting of the Bird Gun and, in addition, there is also a risk that a stabbing operation will be shifted off the target.

Further, since the operator's hands are gripping the Bird Gun's body and probe, it has not been possible to perform even the simple operation of, for example, depressing an image freeze button.

BRIEF SUMMARY OF THE INVENTION

One object of the present invention is to provide an ultrasound probe of a simpler structure capable of steadily mounting a centesis instrument thereon.

Another object of the present invention is to provide an ultrasound probe to allow a centesis adaptor of a simpler structure to be positively fitted thereon.

Another object of the present invention is to provide a centesis adaptor of a simpler structure to allow it to be positively fitted in an ultrasound probe.

The ultrasound probe of the present invention has a slot in its grip section, so that a centesis instrument can be steadily put on the slot. This specific structure allows the axis of the centesis instrument to be less displaced relative to the axis of the probe, so that the centesis instrument is not unsteady relative to the ultrasound probe. Further, the centesis instrument ensures readier attachment and detachment to and from the ultrasound probe simply by putting a body of the instrument on the ultrasound probe.

Further, the slot in the probe is V-shaped in cross-section to allow a length of an angular corner of the centesis instrument: to be fitted in the slot of the probe. This specific structure can suppress any axial displacement of the centesis instrument along the slot as well as any unsteady movement of the centesis instrument.

The slot of the probe is so provided as to extend from end to end of the grip section of the probe. With the centesis instrument put on a near-end side of the slot in the probe, the instrument can be slidably moved forwardly along the slot and, by doing so, a centesis needle slightly projecting from the centesis instrument can be readily inserted into a sheath tube of the insertion section of the probe. It is, therefore, not necessary to bend the centesis needle when it is inserted into the sheath tube.

According to the present invention, since the centesis instrument can be supported at two faces on the grip section of the ultrasound probe to allow the axis of the centesis instrument to be less displaced relative to the axis of the probe. Further, the centesis instrument is not unsteady relative to the probe.

Further, according to the present invention, the forward end of the sheath section is hooked in a hook-shaped hole at the insertion section of the probe and the rear end of the sheath tube is fitted in a recess, whereby it is possible to very firmly fix a centesis adaptor to the insertion section of th e probe.

In order to fit the centesis adaptor in the probe structure it is only necessary to provide a hook at the forward end of the centesis adaptor and to provide a recess relative to the rear end side of the insertion section of the probe. As a result, the centesis adaptor can be made simpler in structure, so that it is easier to wash and sterilize the centesis adaptor. Further, the centesis adaptor, being smaller in size, provides no interference with any stabbing operation. Since a button switch for the freezing of an image is provided at the grip, section on the ultrasound probe of the present invention, the operator, while gripping a body of a Bird Gun together with the probe, can depress the freeze button in a simpler operation.

Additional objects and advantages of the invention will be set forth in the description which follows, and in part will be obvious fro m the description, or may be learned by practice of the invention. The objects and advantages of the invention may be realized and obtained by means of the instrumentalities and combinations particularly pointed out hereinbefore.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
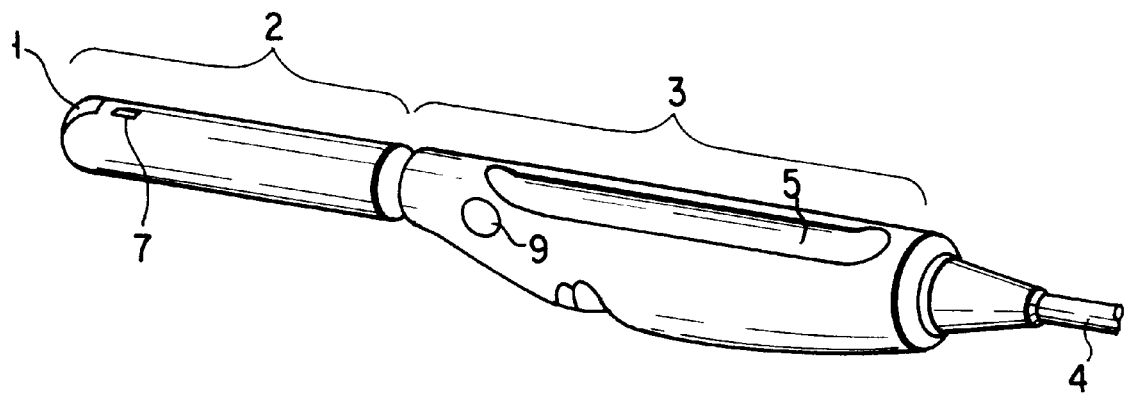
FIG. 1 is an external view showing a conventional ultrasound probe.
Figure 2:
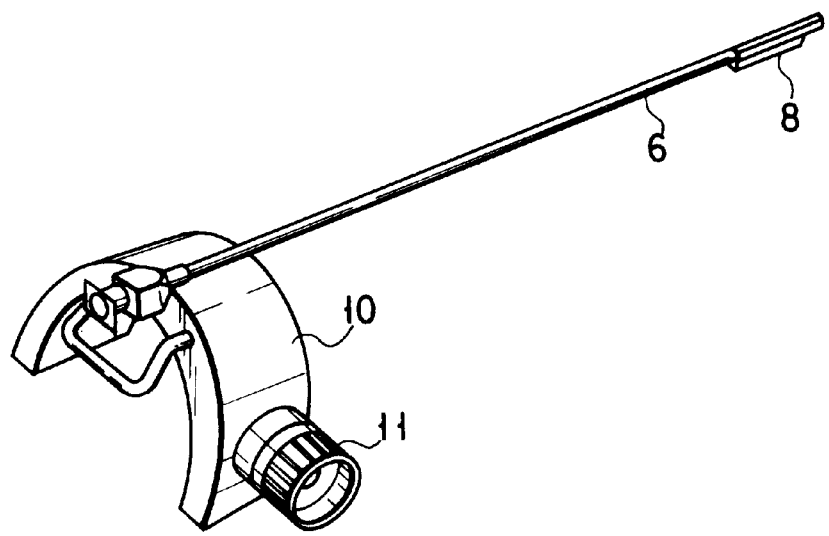
FIG. 2 is an external view showing a conventional centesis adaptor.
Figure 3:
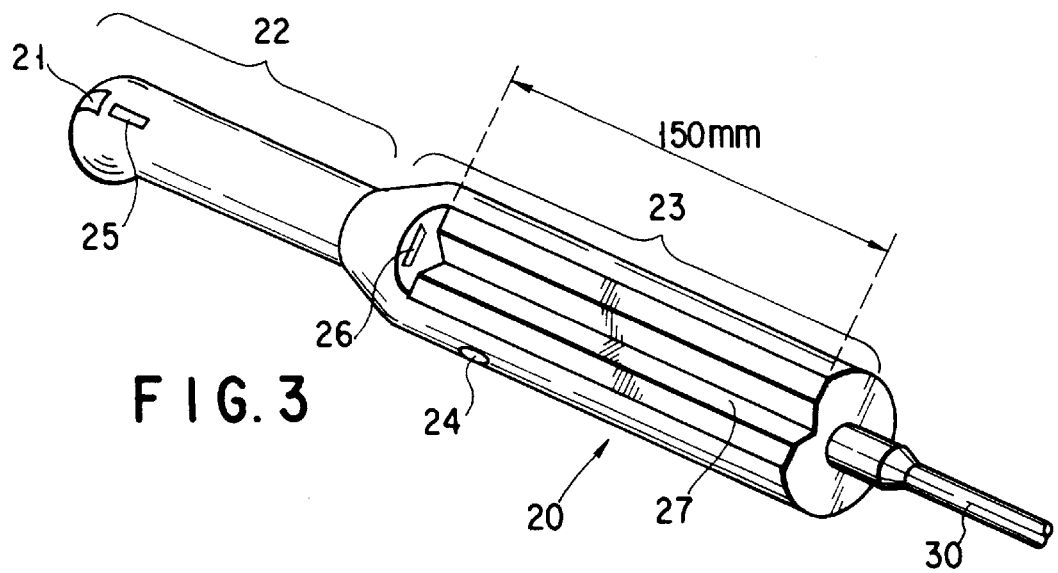
FIG. 3 is an external view showing an ultrasound probe according to a preferred embodiment of the present invention.
Figure 4:
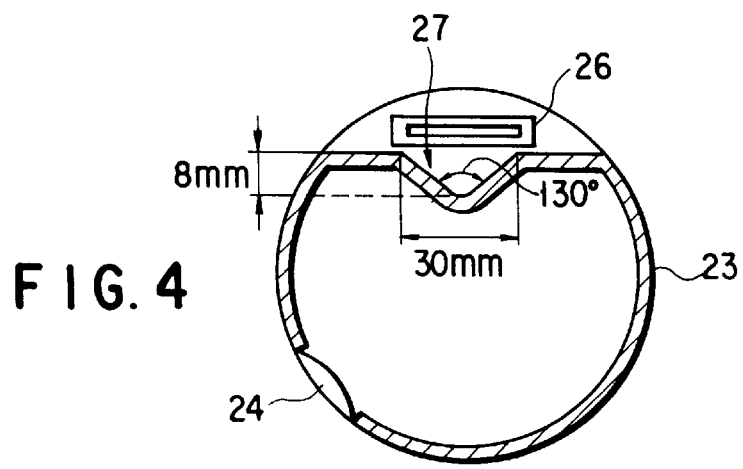
FIG. 4 is a cross-sectional view showing a grip section of an ultrasound probe of the present invention.

With reference to the drawing, an explanation will be given below in conjunction with an ultrasound probe for insertion into a body cavity, by the present invention. FIG. 3 is a view showing an outer appearance of an ultrasound probe according to a present embodiment and FIG. 4 is a cross-sectional view showing a grip section of the ultrasound probe.

An insertion section 22 of hard plastic is provided at a forward end portion of that probe and has a substantially-cylindrical relatively-thin configuration with its cross-section circular, elliptical or flat-elliptical. The insertion section 22 is, therefore, easier to insert into an inside of the human body via a vaginal canal, intestinum rectum, etc., and is germ-proofed. A convex type piezoelectric element array 21 is mounted on the forward end of the insertion section 22 of the probe to allow a visual field as wide as 90° to be acquired. A hole 25 is provided at an upper side of a near-forward end of the insertion section 22 in a way to define a hook-shaped hole extending rearwardly on its part way as shown in FIG. 6B. The hook-shaped hole 25 is provided in a buried metal block 28, such as titanium, of high hardness, taking its durability into consideration.

A grip section 23 of hard plastics is provided at the rear section of the probe 20 and has a relatively-thick cylindrical configuration with its cross-section circular, elliptical or flat-elliptical so that it is easier to grip by the operator or doctor. Further, the grip section 23 of the probe is germ-proofed. The upper side of the substantially cylindrical portion of the grip section 23 is thinly cut off so as for the operator to recognize the upper and lower side of the probe 20 by his or her own feeling of touch without carefully looking at the specific portion of the grip section.

The cut-off section of the grip section has a slot 27, V-shaped in cross-section, extending through the grip section 23 in a parallel relation to an oxial direction of the probe. The slot is about 150 mm long×about 30 mm wide× about 8 mm deep and is opened at a V-shape open angle of about 130°.

A recess 26 is provided in a vertical wall thinly cut off the upper portion of the grip section 23. The recess 26, like the hook-shaped hole 25, is defined in a block formed of a metal, such as titanium, having a high hardness from the standpoint of its durability.

A button switch 24 is provided on a somewhat lower side at a near-forward end section of the grip section 23 to allow an "image freeze" command to be input to the probe by the operator. A signal line from the "image freeze" button switch 24 and signal line from the piezoelectric element array 21 are collected into one cable 30, leading to an ultrasound diagnostic device body, not shown, via a back tail of the grip section 23.

Figure 5:
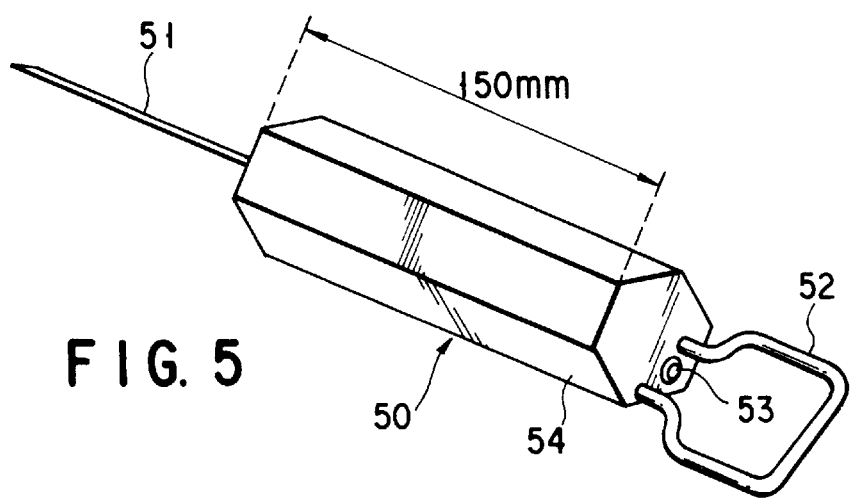
FIG. 5 is an external view showing a Bird Gun.

When a stabbing operation is to be operated, the centesis instrument (Bird Gun) 50 having a body 54 of a substantially hexagonal prism configuration as shown in FIG. 5 is put on the slot 27 of the probe. And this Gun's body 54, together with the grip section 23 of the probe, is gripped by one hand of the operator.

The Bird Gun 50 shown has an outer appearance such that a centesis needle 51 extends out of the forward end of the Gun's body 54. A spring means and associated mechanism are mounted in the Gun's body 54 to allow the centesis needle 51 to be very quickly and forcibly pushed out from the Gun's body and, after being extended out to a full extent, very rapidly pulled back into the Gun's body 54. A handle lever 52 is provided at the rear end of the Gun's body 54, so that the spring means can be squeezed back into the Gun's body 54. When the spring means has been fully squeezed back by the pulling of the handle lever 52, the associated mechanism is locked. A lock release button 53 is also provided at the rear end of the Gun's body.

Figure 6A:
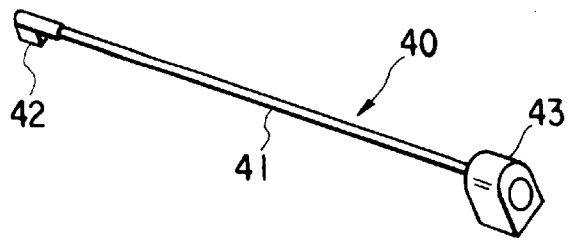
FIG. 6A is an external view showing a centesis adaptor of the present invention.
Figure 6B:
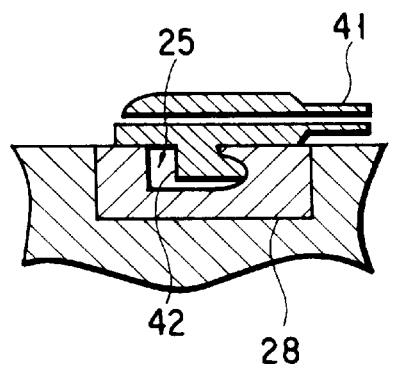
FIG. 6B is a longitudinal view showing a hook-shaped hole provided in an insertion section of the ultrasound probe of the present invention.
Figure 6C:
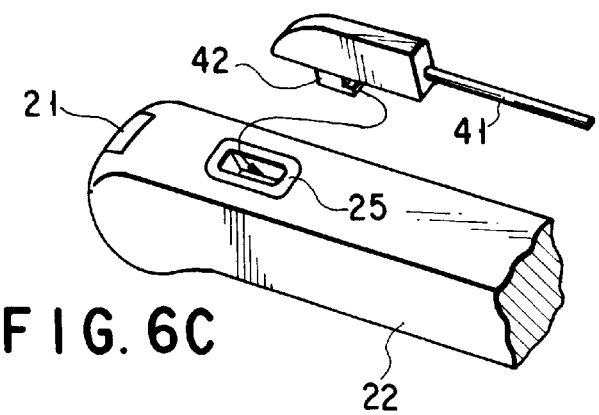
FIG. 6C is a view showing a state in which a hook of the centesis adaptor is latched to the hook-shaped hole.
Figure 6D:
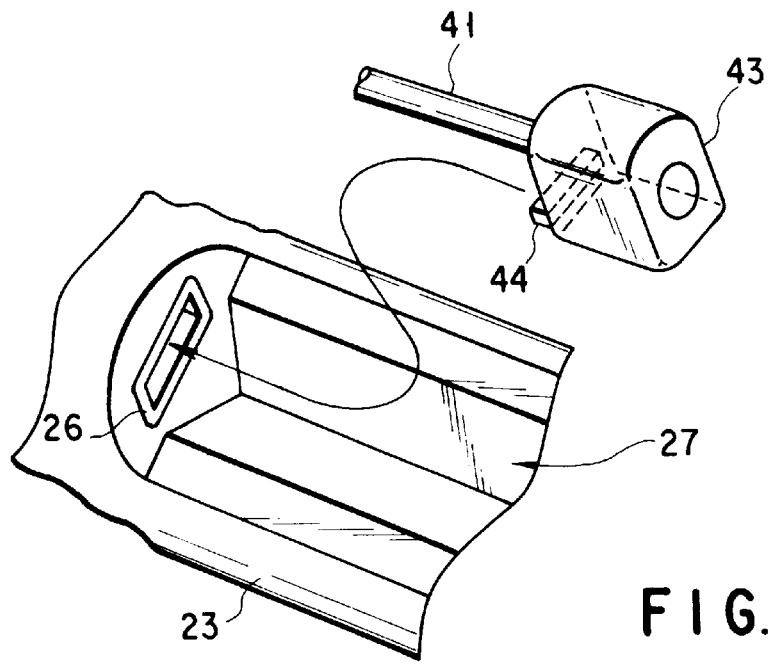
FIG. 6D is a view showing a state in which a projection of the centesis adaptor is fitted in a recess provided in a grip section of the ultrasound probe of the present invention.

FIG. 6A shows an outer appearance of a centesis adaptor 40 so formed as to be adapted to the probe 20. The centesis adaptor 40 has a sheath tube 41 to allow the centesis adaptor 40 to be guided. An engaging hook 42 is provided at the forward end of the sheath tube 41 to be latched to the hook-shaped hole 25 of the probe 20. A projection 44 is provided at the rear end side of the sheath tube 41 to allow it to be fitted in the recess 26 of the probe 20.

The hook 42 of the centesis adaptor 40 is latched to the hook-shaped hole 25 of the probe 20 and the projection 44 of the centesis adaptor 40 is fitted in the recess 26 of the probe 20. By doing so, the centesis adaptor 40 is firmly mounted on the probe 20. The centesis adaptor 40 has a simpler structure and ensures high operability upon washing and sterilization. The probe 20 for mounting the centesis adaptor 40 also has a simpler structure, that is, a hook-shaped hole/recess combination, and also assures high operability upon washing and sterilization. The hook-shaped hole 25 and recess 26 of the probe 20 are defined by the metal, so that they can withstand a repetitive use.

Then when the Bird Gun 50 is to be put on the grip section 23 of the probe 20, firstly the spring means in the body 54 is fully squeezed back into a locking engagement by the pulling back of the spring means in the body 54. At that time, the centesis needle 51 is projected to some extent from the Gun's body 54.

Figure 7:
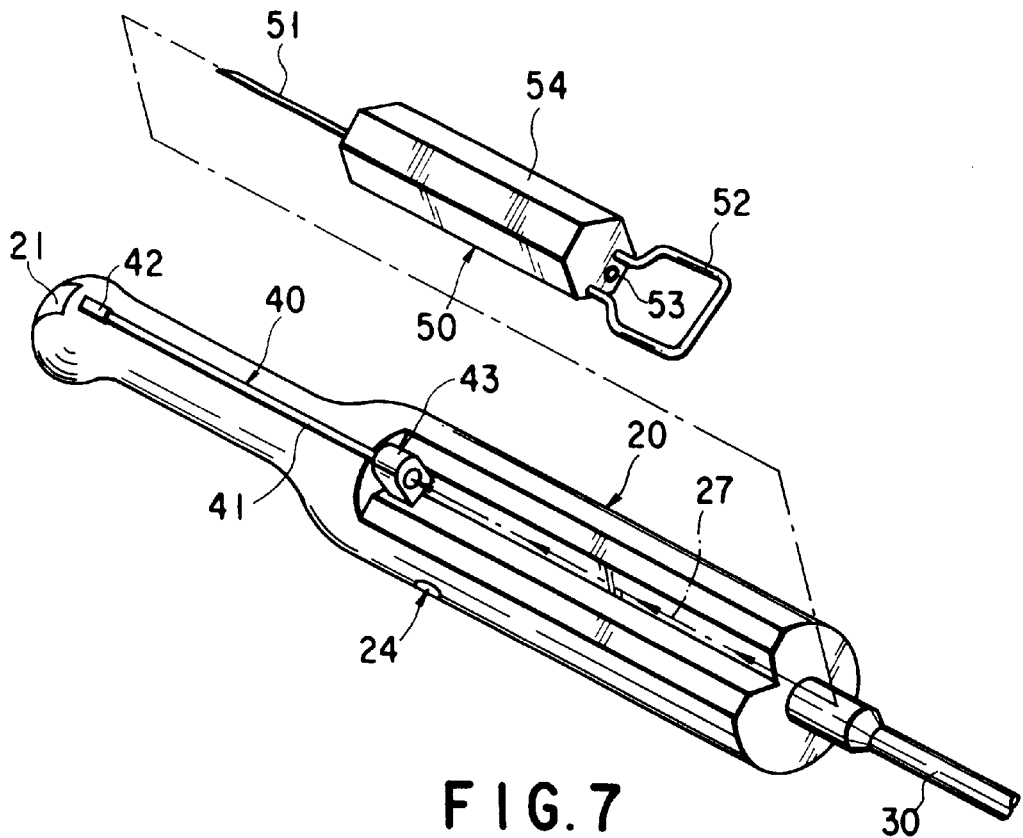
FIG. 7 is a view showing a method for attaching the Bird Gun to the ultrasound probe of the present invention.

Next, as indicated by a dot dash line in FIG. 7, the angular corner of the body 54 of the Bird Gun 50 is put on the V-shaped slot 27 of the grip section 23 in a manner to have the Gun's body 54 overhand from the grip section 23. At this time, the centesis needle 51 projected to some extent from the Gun's body 54 does not interfere with the metal block 43. This is because the slot 27 extend from end to end of the grip section 23 so that the body 54 of the Bird Gun 50 can be placed on the slot 27 in the overhanging state as already set out above.

By slidably moving the body 54 of the Bird Gun 50 forwardly on and long the slot 27 of the probe, the centesis needle 51 extending to some extent from the body 54 of the Bird Gun is guided into the sheath tube 41 of the centesis adapter 40. Since the tip of the centesis needle 51 is automatically inserted into the sheath tube 41 of the centesis adaptor 40 in a way to be assisted by the guiding function of the slot 27, there is no cumbersome operation like threading a yarn into the eye of a needle.

Figure 8:
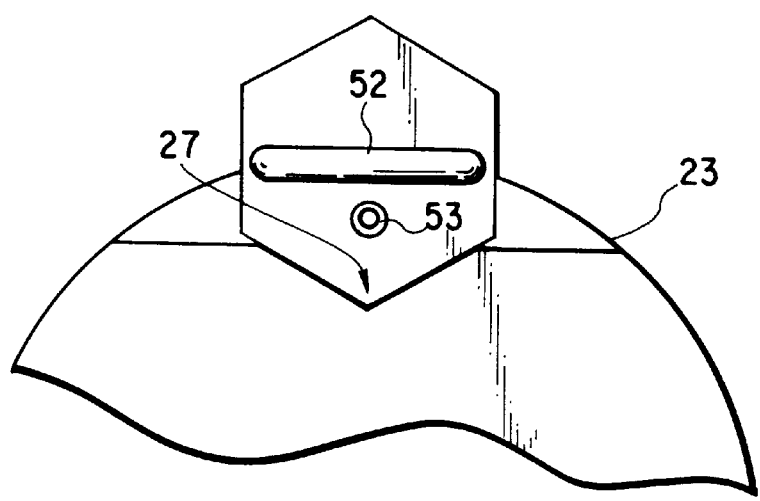
FIG. 8 is a view as seen from a rear end of the grip section of the ultrasound probe with the Bird Gun attached thereto.
Figure 9:
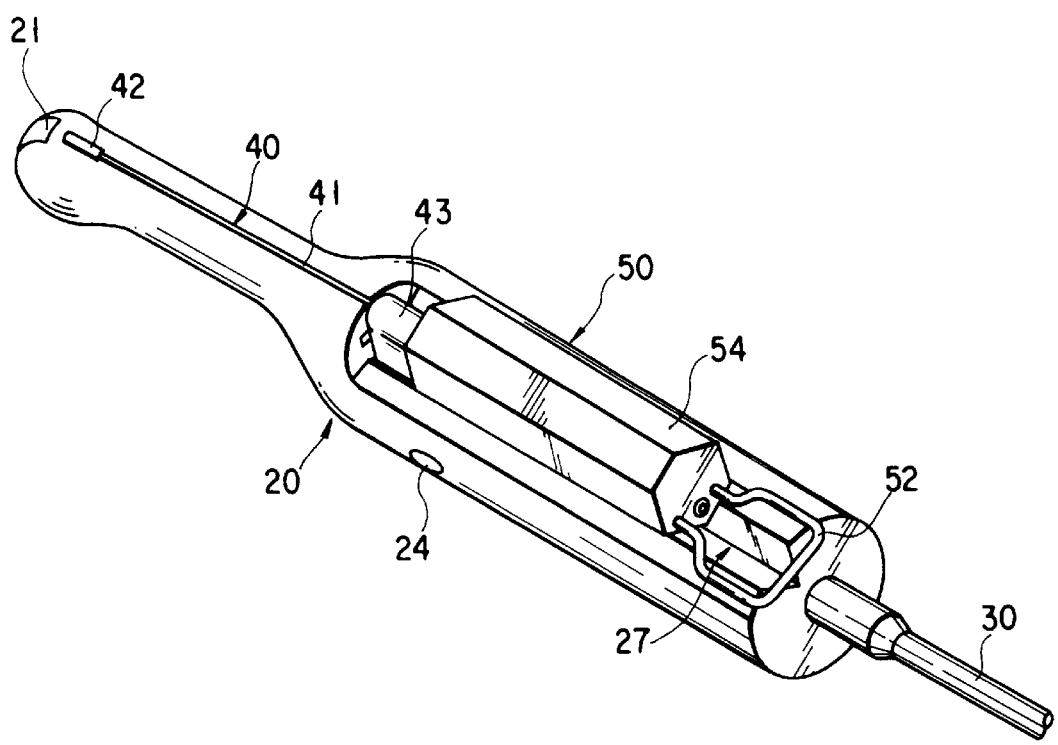
FIG. 9 is an external view showing a state in which the centesis adaptor and Bird Gun are attached to the ultrasound probe of the present invention.

By these simpler operations the centesis adaptor 40 and Bird Gun 50 can be set on the probe as shown in FIGS. 8 and 9.

In an actual stabbing operation, the operator grips the body 54 of the Bird Gun 50, together with the grip section 23 of the probe 20, by one hand. Since the angular corner defined by the two adjacent faces of the hexagonally prismatic body 54 of the Bird Gun 50 is supported by the two adjacent faces of the V-shape cross-sectional slot, the axis of the Bird Gun 50 is less displaced relative to the axis of the probe, so that the Gun's body 54 is not unsteady relative to the grip section 23 to allow the Gun's body 54 and probe 20 to be steadily grasped by the operator's one hand.

And the operator inserts, together with the centesis adaptor 40, the insertion section 22 of the probe 20 into the body cavity of the human subject and, looking at an ultrasound image, aims the centesis needle at a target in the human body. At this time, the operator depresses the button switch 24, as required, to freeze an ultrasound image involved. In this operation, the operator, gripping the grip section 23 of the probe by his or her underhand, that is, with the back of his or her hand down, can simply depress the buttom switch 24 by moving his or her thumb.

And the operator adjusts the sight of the Bird Gun 50 so as to aim it at the target and depresses a trigger button 50. By doing so, the spring means of the Bird Gun 50 is unlocked, this quickly darting the centesis needle 51 from the Gun's body 54 into a target tissue of the human subject and quickly pulling it back with a tissue sample deposited in the centesis needle.

The present invention is not restricted to the above-mentioned embodiment and can be variously changed or modified without departing from the spirit and scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

I claim:

1. An ultrasound probe for insertion into a body cavity comprising:
    a rod-like grip section constituting a rear section of the ultrasound probe; and
    a rod-like insertion section of the ultrasound probe constituting a forward section of the ultrasound probe which is equipped at a forward end with a piezoelectric element array,
    wherein said grip section has a slot structure so formed as to extend parallel to an axis of the ultrasound probe.

2. An ultrasound probe according to claim 1, wherein the slot structure is so formed as to have a V-shape in cross-section.

3. An ultrasound probe according to claim 2, wherein a V-shape open angle of the slot structure is substantially 130°.

4. An ultrasound probe according to claim 2, wherein the slot structure has a width of substantially 30 mm.

5. An ultrasound probe according to claim 2, wherein the slot structure has a depth of substantially 8 mm.

6. An ultrasound probe according to claim 1, wherein the slot structure is formed to an end of the grip section.

7. An ultrasound probe usable with a centesis instrument including a body having a built-in mechanism for dynamically moving a centesis needle back and forth, comprising:
    a rod-like grip section constituting a rear section of the ultrasound probe; and
    a rod-like insertion section constituting a forward section of the probe and having a piezoelectric element array at a forward end of the insertion section, wherein said grip section has a slot structure formed parallel to an axis of the probe to allow the body of the centesis instrument to be put on the grip section.

8. An ultrasound probe usable with a centesis instrument including a body having a built-in mechanism for dynamically moving a centesis needle back and forth, comprising:

a rod-like grip section constituting a rear section of the ultrasound probe; and a rod-like insertion section constituting a forward section of the ultrasound probe and having a piezoelectric element array at a forward end, wherein said grip section has a slot structure which, in order to allow the body of the centesis instrument to be put on the grip section of the probe, is formed at the grip section of the probe to support the body of the instrument on two faces thereof.

9. An ultrasound probe which can mount a sheath tube thereon to guide a centesis needle, comprising:

a rod-like grip section constituting a rear section of the ultrasound probe;

a rod-like insertion section constituting a forward section of the probe and having a piezoelectric element array at a forward end;

a hook-shaped hole structure which, in order to allow a forward end of the sheath tube to be hooked therein, is provided near to the forward end of the insertion section; and a recess structure provided near to a rear end side of the insertion section to retain the rear end of the sheath tube in place.

10. An ultrasound probe according to claim 9, wherein the hook-shaped hole structure and recess structure each are defined of a metal.

11. A centesis adaptor comprising:

a sheath tube for guiding a centesis needle;

an engaging hook provided near to a forward end of the sheath tube; and a projection provided near to a rear end of the sheath tube.

12. An ultrasound probe comprising:

a rod-like grip section constituting a rear section of the probe;

a rod-like insertion section constituting a forward section of the probe and having a piezoelectric element array at a forward end; and a button switch provided at the grip section to obtain a frozen image.

13. An ultrasound probe according to claim 12, wherein the button switch is provided at a place below a horizontal cross-section surface of the grip section.

14. An ultrasound probe according to claim 12, wherein the button switch is provided near to the forward section side of the grip section.

* * * * *